US005257986A

United States Patent [19]

Herbert et al.

[11] Patent Number: 5,257,986

[45] Date of Patent: Nov. 2, 1993

[54] CONTAINER FOR THE SEPARATE STERILE STORAGE OF AT LEAST TWO SUBSTANCES AND FOR MIXING SAID SUBSTANCES

[75] Inventors: Reinhold Herbert, Neu-Anspach; Klaus Sommermeyer, Rosbach, both of Fed. Rep. of Germany

[73] Assignee: Fresenius AG, Bad Homburg, Fed. Rep. of Germany

[21] Appl. No.: 477,878

[22] PCT Filed: Oct. 10, 1989

[86] PCT No.: PCT/DE89/00646

§ 371 Date: Jun. 5, 1991

§ 102(e) Date: Jun. 5, 1991

[87] PCT Pub. No.: WO90/03775

PCT Pub. Date: Apr. 19, 1990

[30] Foreign Application Priority Data

Oct. 11, 1988 [DE] Fed. Rep. of Germany ....... 3834566

[51] Int. Cl.$^5$ .............................................. A61B 19/00

[52] U.S. Cl. .................................... 604/416; 604/403; 604/411

[58] Field of Search ................ 206/222, 219; 604/413, 604/416, 410, 403, 411

[56] References Cited

U.S. PATENT DOCUMENTS

| | | | |
|---|---|---|---|
| 4,484,920 | 11/1984 | Kaufman et al. | 604/416 |
| 4,515,586 | 5/1985 | Mendenhall et al. | 604/87 |
| 4,548,606 | 10/1985 | Larkin | 604/414 |
| 4,550,825 | 11/1985 | Sutryn et al. | 206/222 |
| 4,589,879 | 5/1986 | Pearson | 604/411 |
| 4,781,679 | 11/1988 | Larkin | 604/88 |
| 4,871,354 | 10/1989 | Conn et al. | 604/89 |
| 4,927,013 | 5/1990 | Van Brunt et al. | 206/221 |

*Primary Examiner*—Robert A. Hafer
*Assistant Examiner*—Sam Rimell
*Attorney, Agent, or Firm*—Jack Schuman

[57] ABSTRACT

A container (1) is described for the separate sterile storage of at least two substances and for mixing said substances. Said container comprises a first chamber (2) for storage of a powdery substance (17) and a second chamber (3) for storage of a liquid. While said second chamber (3) preferably consists of polymer layers, chamber (2) is manufactured from a rigid material, prefeably polycarbonate, hard-PVC or polypropylene. Both chambers are connected via the tubular section (10) which is closed by the break-off part (4). For mixing both substances the break-off part (4) is broken off along the weakened line (7). The mixture is taken off through the outlet opening (6). A separate storage of two substances and the sterile mixing of said substances is possible by means of the container (1).

8 Claims, 2 Drawing Sheets

Figure 1:
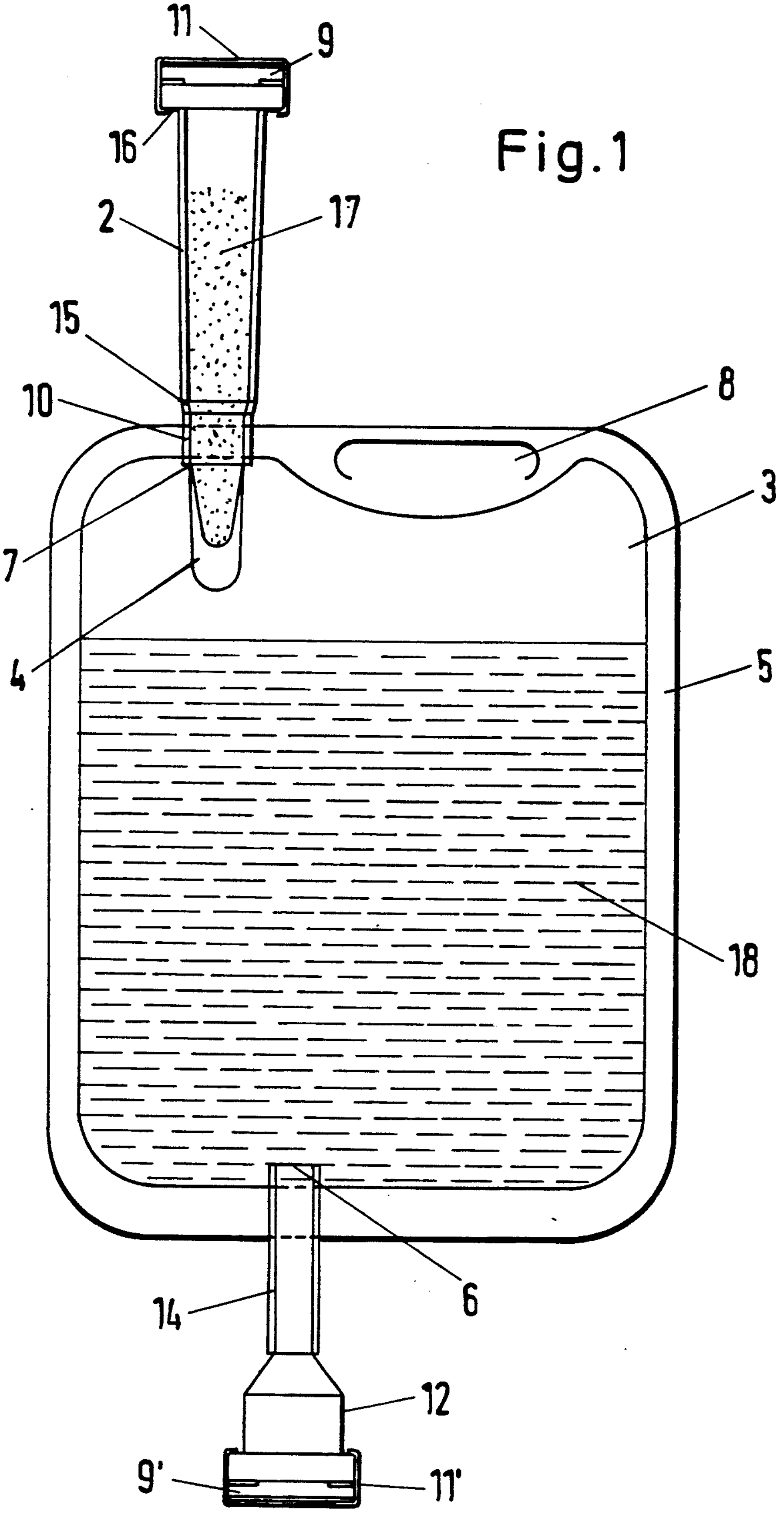

CONTAINER FOR THE SEPARATE STERILE STORAGE OF AT LEAST TWO SUBSTANCES AND FOR MIXING SAID SUBSTANCES

This invention relates to a container for the separate sterile storage of at least two substances and for mixing said substances, the container including a first chamber as well as a second chamber which communicates with said first chamber and consists especially of a bag made of a thermoplastic material.

The present invention also relates to a sterile, medical mixing assembly comprising at least one first chamber which is closed on all sides and contains a first substance, and a second chamber, in particular a plastic bag containing a second substance, in particular an aqueous solution, said chambers being adapted to be brought into flow communication for mixing purposes, and to a method for the manufacture thereof.

Medical storage bags are inter alia used for storing infusion solutions and must therefore be heat-sterilizable above 100° C. to satisfy the normal hygienic demands. Bags of this type are e.g. known from German patent specification 32 00 264 or German patent specification 33 05 365.

However, these known bags made of a plastic foil only comprise one chamber, so that they are merely suited for storing infusion solutions that do not lose their potency or strength when stored over a long period of time.

For special therapies, however, there are infusion solutions which can only be prepared shortly before infusion on account of their extremely low storage stability, with two different substances being intermixed as a rule.

These two substances may be liquid components which are mixed prior to infusion, or powdery medicaments, such as antibiotics or cytostatic agents which are dissolved in a carrier solution, such as an aqueous saline solution.

Bags which are made on the basis of the above-mentioned storage bags are known to be used for storing and subsequently mixing a liquid active substance and a carrier fluid. These bags are welded in the center to form two chambers, a tubular member and a break-off part closing the tubular member being arranged in the weld as a connection between the two chambers. Prior to infusion the break-off part is broken off and subsequently falls into the interior of the one chamber. The liquid may then flow from the one chamber into the second one, with the necessary sterility being ensured.

Such an infusion bag which consists of two chambers is also known from German utility model 77 19 528. Several infusion solutions can be stored separately in this infusion bag and applied. The two chambers are separated from each other by welds having arranged therein a breakable tube which can be opened easily and is divided into several parts.

There are however several reasons why these known bags cannot be used for storing a powdery component and a liquid component and for subsequently mixing the same. On the one hand, it is a lot more expensive and difficult to fill a bag with a powder than with a liquid. On the other hand, it is not possible to pass the powder from the one bag chamber into the other one without any remainders being left.

Although there is the possibility of passing the liquid into the respectively other chamber containing the powder, this is not advantageous for all substances.

Another problem resides in the fact that, on account of the necessary sterilization of the plastic bag, water vapour cannot be prevented from passing through the bag wall into the interior of the bag. Moreover, the inner sides of most bags inseparably stick to one another during sterilization without any filling. Since the powder which may e.g. be an antibiotic or cytostatic agent and can only be filled into the container after heat sterilization must be stored in the container in a dry state, it would be necessary in another production step to remove the diffused water again, which would entail corresponding costs.

For this reason powdery medicaments have so far been stored in gas bottles and introduced into the liquid stored in a bag prior to infusion. However, since this operation must be carried out under sterile conditions, special precautionary measures must again be taken. So far a nurse could e.g. not prepare the infusion solution at the patient's bed. Moreover, the person pouring the substance out of the glass bottle might get hurt.

It is therefore the object of the present invention to provide a container and a mixing assembly which make it possible to store two media of different consistence under sterile conditions and to mix the same under sterile conditions in a simple way.

This object is attained with a container in which the first chamber is made of a substantially rigid material and includes a tubular section whose end portion is closed and formed as a break-off part. The tubular section is arranged in the edge of the second chamber in such a way that the break-off part is positioned in the interior of the bag. Advantageous developments are the subject matter of the subclaims.

The mixing assembly of the invention comprises a first chamber which is made of a substantially rigid material and includes a tubular section whose end portion is closed and formed as a break-off part. The tubular section is so welded into the edge of the bag that the break-off part is positioned in the interior of the bag and releases the first substance for filling into the first chamber after having been broken off.

The first substance may be a powder or a sterile-filtered medicinal substance solution.

For producing the sterile mixing assembly the container of the invention is first manufactured and the first chamber is then closed. The whole container is subsequently subjected to radiation sterilization with e— or $\gamma$ rays. This presterilization is of special importance to the first chamber.

The aqueous solution or carrier solution is then filled into the second chamber and the same is closed. The whole container is subsequently subjected to heat sterilization, the closed first chamber being poststerilized at the same time. Since the rigid material of the first chamber preferably consists of polycarbonate, hard PVC or polypropylene, there is no risk that any liquid enters into the first chamber and thus destroys the powdery material.

The first chamber can subsequently be opened, with the sterile conditions being maintained, and a powdery medicament may be filled under sterile conditions, e.g. laminar flow, into the first chamber which is then closed by a sterile plug. For the safe, sterile introduction of the container into the powder filling area, the preceding heat sterilization may be carried out with a surrounding bag which is removed during the introduction operation. The entire bag is thus sterile on the outside. Such a filling method is of particular advantage to those powdery pharmaceutical substances that are heat-sensitive and can only be filled at room temperature.

In another embodiment it is also possible to fill a sterile-filtered medicinal substance solution into this rigid and already sterile chamber at room temperature, a tightly sealing cover being subsequently mounted thereon.

The container which is filled and sterilized in this way can be directly hung at the sick bed where a nurse or physician must only break off the break-off part prior to infusion to bring the two substances into contact with each other. The break-off part falls into the second chamber and simultaneously releases the connection opening for the first chamber arranged thereabove, so that the powdery or liquid medicament slips downwards into the second chamber without any additional operations being required and, what is most important, under sterile conditions. Since the first chamber is made of a rigid material and preferably shaped like a funnel, it is ensured that no powdery material remains in the first chamber. Moreover, the first chamber can be rinsed with the carrier solution.

After the substances have been mixed with each other and dissolved, a corresponding infusion tube is connected to the outlet opening which is provided with a diaphragm and a cap or a piercable insert.

The tubular section establishing the connection between the first and second chambers, and the break-off part are preferably made of the same material as the first chamber. The tubular section is preferably welded into the edge of the second chamber, which consists of a plastic bag. The material of the tubular section may here be welded either directly with the bag material or through an intermediate layer of an addition welding material (e.g. according to German patent specification 33 05 365).

Depending on the type of the medicament or the carrier solution, the first chamber has a capacity of from 2 to 50 ml and the second chamber a capacity of from 50 to 250 ml.

Embodiments of the invention will now be described in more detail by way of example with reference to the drawing, in which FIG. 1 shows a view on the mixing assembly of the invention, and FIGS. 2A, 2B, 2C, 2D each show details of another embodiment of the first chamber.

The mixing assembly will now be described with reference to FIG. 1:

Container 1 of the invention comprises a first chamber 2 and a second chamber 3. The chamber serves to receive the powdery substance 17 and is closed by a plug 9 and a flanged cap 11. On the other hand, a closure may also be firmly welded to edge 16. Chamber 2 is on the whole of a funnel-like configuration and passes with its conically convergent end 15 into the tubular section 10 which is closed at its bottom end by the break-off part 4. The tubular section 10 is welded into the welding edge 5 of the second chamber 3. This second chamber 3 is preferably made of a plastic foil and contains the carrier solution 18. This plastic bag 3 comprises a hanging means 8 at its upper end. Outlet opening 6 is positioned at the bottom end of this bag.

Another tubular section 14 or a hose which is closed at the lower end by means of a conventional connection member 12 including a plug 9' and a cap 11' is inserted into the outlet opening 6.

For filling the powdery substance 17 into bag 3 it is only necessary to break off the break-off part 4 along the weakened line 7. The powdery substance 17 will then slip automatically into chamber 3 where it is mixed with the carrier solution 18.

Another embodiment of the first chamber 2 of the invention is illustrated in individual FIGS. 2*a*, 2*b*, 2*c*, and 2*d*). Same parts as those in the assembly shown in FIG. 1 are provided with the same reference numerals. In the second embodiment the closing element is shaped in the form of a piston 19 which is displaceably supported on the second chamber 2 and provided with an O-ring seal 22. In the sealing position shown in FIG. 2*a* the piston is in sealing engagement with the tubular section 10 and comprises a piston rod 20 which extends through the interior of the first chamber 2. The upper end of the first chamber 2 is closed by means of an elastic wall 21 which is held by a holding ring 23 on an upper flange of the first chamber 2. The piston rod 20 extends up to the bottom side of the elastic wall 21.

Figure 2A:
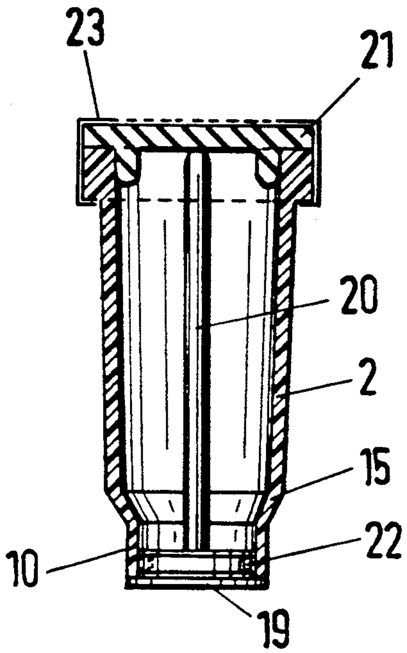
Figure 2B:
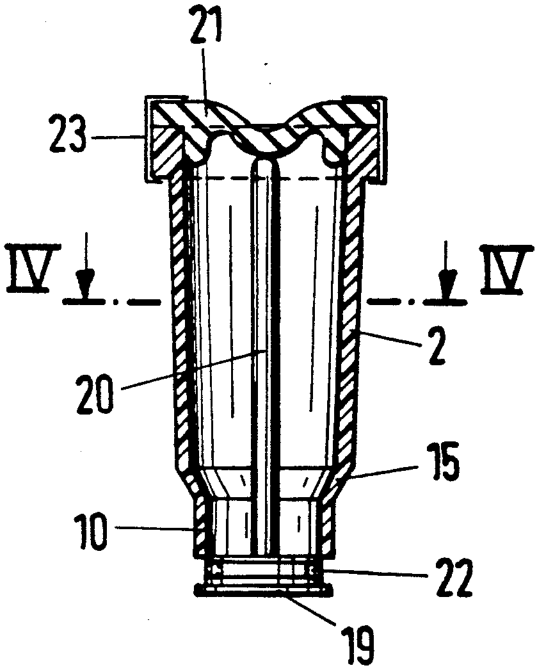

The opened position of the first chamber 2 is illustrated in FIG. 2*b* from which it becomes apparent that piston 19 and piston rod 20 connected thereto are displaceable into the open position by virtue of an elastic, manually effected deformation of the elastic wall 21. Piston rod 20 is guided (not shown) in the first chamber 2, e.g. by means of a separate spacer element which simultaneously acts as a securing means to prevent piston 19 from falling out of the first chamber 2 in the opened position.

Figure 2C:
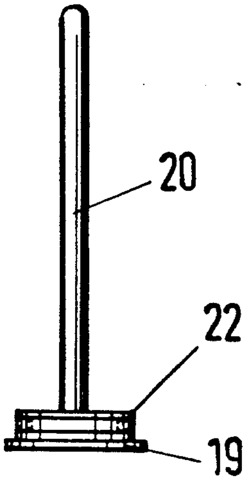

FIG. 2*c* shows details of the closing piston 19 and of the O-ring seal 22 and piston rod 20.

Figure 2D:
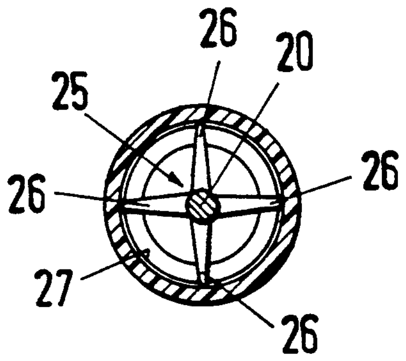

It becomes apparent from FIG. 2*d* that rod 20 may be provided with a spacer 25 which in the embodiment may consist of four arms 26 which are arranged in star-shaped configuration and face radially outwards and may be supported on the inner wall 27 of the cylindrical main part 2 of container 2. A certain frictional force is here applied for reliably holding piston 19 in its closing and opening positions.

The closure means 1 of the invention can be produced in a very simple way and operated in a reliable manner. If necessary, it is moreover possible to return piston 19 from its opening position shown in FIG. 2 into its closing position. Pressure must here be exerted on the end flange 16 which prevents any damage to the sealing portion 15, as it radially overlaps the same at the outside.

We claim:

1. Apparatus for the separate sterile storage of at least two substances, in which apparatus said substances can be mixed, and from which apparatus said mixed substances can be dispensed for use, said apparatus comprising:

(a) a first container adapted to contain a first substance and made of substantially rigid weldable plastic material, said first container being of unitary one-piece construction having a first end terminating in a hollow generally tubular section having a removable portion integral therewith adapted to be broken away from said tubular section thereby to provide a first opening through the wall of said first container, said first container having a second end opposite said first end with a second opening through which second opening said first substance may be introduced into said first container, (b) a scored line extending around said tubular section and interposed between the removable portion of said tubular section and the rest of said tubular section to facilitate breaking away said removable portion from said tubular section,
(c) means to close said second opening,
(d) a second container made of thin flexible weldable thermoplastic material and adapted to contain a second substance,
(e) the first end of said first container being welded to the wall of said second container to make a fluid-tight connection therebetween, said tubular section and the removable portion thereof extending into said second container,
(f) that portion of said first container including said tubular section and the removable portion thereon which extends into said second container being totally imperforate,
(g) whereby, upon force being applied through the thin flexible wall of said second container, the removable portion of said tubular section may be broken away therefrom, thereby to permit said first substance to enter said second container through said first opening and mix with said second substance,
(h) dispensing means mounted in the lower portion of said second container through which said mixed first and second substances may be dispensed for use.

2. Apparatus as in claim 1, wherein:
(g) said first container is made of polycarbonate, polyvinyl chloride or polypropylene.

3. Apparatus as in claim 1, wherein:
(g) said second container is made from polyolefins.

4. Apparatus as in claim 1, wherein:
(g) said second container is made from polyethylene, polypropylene, poly-n-butylene, polyisobutylene, poly-4-methylpentene-1, chlorosulphonated polyethylene, polystyrene, halogenated polyethylenes, polymethyl methacrylate, and copolymers thereof.

5. Apparatus as in claim 1, wherein:
(g) the volume of said first container is approximately 2–50 ml.

6. Apparatus as in claim 1, wherein:
(g) the volume of said second container is approximately 50–250 ml.

7. Apparatus as in claim 1, wherein:
(g) the volume of said first container is approximately 2–50 ml.,
(h) the volume of said second container is approximately 50–250 ml.

8. Apparatus as in claim 1, wherein:
(g) said dispensing means comprises a pierceable closure.

* * * * *